(12) United States Patent
Pages

(10) Patent No.: US 9,733,270 B2
(45) Date of Patent: Aug. 15, 2017

(54) GARMENT INCORPORATING A NON DESTRUCTIVE CONTROL SYSTEM

(75) Inventor: Marion Pages, Toulouse (FR)

(73) Assignee: EUROPEAN AERONAUTIC DEFENCE AND SPACE COMPANY EADS FRANCE, Paris (FR)

( * ) Notice: Subject to any disclaimer, the term of this patent is extended or adjusted under 35 U.S.C. 154(b) by 1091 days.

(21) Appl. No.: 13/701,038

(22) PCT Filed: May 31, 2011

(86) PCT No.: PCT/EP2011/058962
§ 371 (c)(1),
(2), (4) Date: Dec. 20, 2012

(87) PCT Pub. No.: WO2011/151332
PCT Pub. Date: Dec. 8, 2011

(65) Prior Publication Data
US 2013/0106403 A1 May 2, 2013

(30) Foreign Application Priority Data

Jun. 1, 2010 (FR) ...................................... 10 54265

(51) Int. Cl.
*G01R 1/04* (2006.01)
*G01N 27/90* (2006.01)
(Continued)

(52) U.S. Cl.
CPC ......... *G01R 1/0416* (2013.01); *G01N 27/902* (2013.01); *G01N 29/226* (2013.01); *G01N 33/367* (2013.01)

(58) Field of Classification Search
CPC .. G01R 1/0416; G01N 27/902; G01N 33/367; G01N 29/226
See application file for complete search history.

(56) References Cited

U.S. PATENT DOCUMENTS

| 5,211,321 | A | * | 5/1993 | Rodriguez | ......... A41D 13/0012 2/102 |
| 5,416,310 | A | * | 5/1995 | Little | ................. G06K 7/10881 2/102 |
| 5,555,490 | A | | 9/1996 | Carroll | |
| 5,694,939 | A | * | 12/1997 | Cowings | .............. A61B 5/0205 128/905 |
| 6,243,870 | B1 | | 6/2001 | Graber | |
| 6,324,053 | B1 | | 11/2001 | Kamijo | |
| 6,563,424 | B1 | | 5/2003 | Kaario | |

(Continued)

FOREIGN PATENT DOCUMENTS

| EP | 1 213 560 A1 | 6/2002 |
| FR | 2 874 689 A1 | 3/2006 |

OTHER PUBLICATIONS

Thomas Mestl et al.: "Mobile Worker: ICT Solutions for the Surveyor", Det Norske Veritas, XX, XX, No. 99-2043, Jan. 11, 2000 (Jan. 11, 2000), pp. 1-82, XP002181238, paragraphs [06.1L [06.2], Cited in ISR.

(Continued)

*Primary Examiner* — Patrick Assouad
*Assistant Examiner* — Haidong Zhang
(74) *Attorney, Agent, or Firm* — Young & Thompson

(57) ABSTRACT

A garment of vest type (1) incorporating a non-destructive control system includes, as constituent elements, an electronic measurement device (26) able to be connected to a measurement sensor, and linked to an electronic card (20) itself linked to an electrical power supply source (21) and to a viewing and control screen (27), and cables for electrically and electronically linking the constituent elements to one another.

18 Claims, 2 Drawing Sheets

(51) Int. Cl.
*G01N 29/22* (2006.01)
*G01N 33/36* (2006.01)

(56) References Cited

U.S. PATENT DOCUMENTS

| | | | |
|---|---|---|---|
| 6,687,523 B1 * | 2/2004 | Jayaramen et al. | A41D 13/1281 600/388 |
| 2006/0283908 A1 * | 12/2006 | Sticker | A45F 5/02 224/684 |
| 2007/0139875 A1 * | 6/2007 | Carstens | G06F 1/163 361/679.01 |
| 2008/0170471 A1 * | 7/2008 | Rolet | G01S 5/30 367/127 |
| 2009/0229361 A1 | 9/2009 | Mengeling et al. | |

OTHER PUBLICATIONS

Dudziak M et al.: "Nondestructive evaluation for crack, corrosion, and stress detection for metal assemblies and structures", Proceedings of the International Society for Optical Engineering (SPIE), SPIE, USA, vol. 3586, Jan. 1, 1999 (Jan. 1, 1999), pp. 20-31, XP009142690, ISSN: 0277-786X paragraph [0004], Cited in ISR.

S. J. Schwartz, et al.: "The smart vest: towards a next generation wearable computing platform", vol. technical report nr. 504 Jul. 1999 (Jul. 1999), pp. 1-7, XP002614614, Retrieved from the Internet: URL:http://pubs.media.mit.edu/pubs/papers/TR-504.pdf [retrieved on Dec. 17, 2010] the whole document, Cited in ISR.

Paul Lukowicz et al.: "The WearARM Modular, Low-Power Computing Core", IEEE Micro, vol. 21, No. 23, May 2001 (May 2001)-Jun. 2001 (Jun. 2001), pp. 16-28, XP002614615, DOI: 10.1109/40.928762 pp. 22,26,27 pp. 18,19,21; figure 2, Cited in ISR.

Sunkpho J et al.: "MIA: a wearable computer for bridge inspectors", Wearable Computers, 1998. Digest of Papers. Second International Symposium on Pittsburgh, PA, USA Oct. 19-20, 1998, Los Alamitos, CA, USA, IEEE Comput. Soc, US, Oct. 19, 1998 (Oct. 19, 1998), pp. 160-161, XP010312829, DOI: DOI:10.1109/ISWC. 1998.729545 ISBN: 978-0-8186-9074-7 the whole document, Cited in ISR.

International Search Report, dated Jul. 11, 2011, from corresponding PCT application.

* cited by examiner

GARMENT INCORPORATING A NON DESTRUCTIVE CONTROL SYSTEM

This invention falls within the field of non-destructive testing, and more generally of maintenance. It relates more specifically to a garment incorporating all the functions required for non-destructive testing.

BACKGROUND OF THE INVENTION

The garment according to the invention finds application in all the fields in which it is necessary to carry out tests, on parts or all types of materials, using non-destructive technologies, e.g. thickness measurements, corrosion detection tests, etc. The aeronautics, aerospace, construction, civil engineering, nuclear and naval fields can be cited in particular, this list being in no way exhaustive.

SUMMARY OF THE INVENTION

In such fields, in order to carry out the non-destructive testing the operators must frequently travel great distances and/or move in areas difficult to access. In the aeronautics field in particular, inspection operations on the final assembly lines, whose dimensions are increasingly large, require traveling great distances. Some inspection operations in areas difficult to access, such as an aircraft's tail, require the use of harnesses to bring the operator to the area where the test must be carried out. The same is true, for example, for the inspection of launchers in the aerospace field, or even of bridges in the construction and civil engineering sector. In other cases, the inspection must be carried out in areas that are difficult to access because they are very confined and narrow, e.g. in manholes.

The existing non-destructive testing systems typically comprise a plurality of elements, principally an electronic measurement module linked to one or more measurement sensors, which permits non-destructive measurements, of a predefined type according to the application envisaged, to be taken, e.g. by ultrasound or by eddy currents; an electronic card, or motherboard, for generating control signals towards the measurement module, and for receiving and processing signals transferred from the latter; an electrical power supply source and a viewing and control screen, these various elements being linked operationally to one another by electrical and electronic connecting cables. This equipment is cumbersome, heavy (of the order of 6 to 10 kg) and not very suitable for mobile use.

Currently all of this equipment is transported by the operator either in cases or by hand. For the actual inspection, the operator is frequently compelled to carry the equipment with one arm, the other arm being used to hold the measurement sensor and to adjust parameters. It is easy to understand that, in certain environmental conditions, the operator's task is thus difficult and uncomfortable. In extreme cases, this hinders the very quality of the inspection.

This invention aims to improve the working conditions for non-destructive testing operators and consequently both the quality of the inspections and the safety of the operators and thus, generally, safety in the field in question, e.g. the aeronautics field.

Non-destructive testing is defined in a conventional way in this description, i.e. as a test carried out on parts or structures external to the operator, and intended to provide information about the health of these parts or structures, more specifically about their integrity and/or their compliance with material quality requirements, without resulting in alterations potentially harmful to their subsequent use. Non-destructive testing thus makes it possible to highlight defects likely to affect the availability, safety of use and, more generally, the compliance of the part or structure with its intended use. As an example, the non-destructive testing system according to the invention thus makes it possible to identify defects not visible on the parts, such as cracks, delaminations in composite materials, bonding defects between the parts, or a porosity defect for a resin in a composite material.

Non-destructive testing according to this invention utilizes a handheld non-destructive measurement sensor for taking the measurements.

To this end, according to the invention a system is proposed for the non-destructive testing of a part, which comprises as constituent elements, in a way that is standard in itself, a non-destructive electronic measurement device able to be connected to a non-destructive measurement sensor, which is of the type intended to be held in the hand for taking test measurements, and linked to an electronic control card itself linked to an electrical power supply source and to a viewing and control screen, and connecting cables for electrically and electronically linking said constituent elements to one another. These constituent elements and these connecting cables are incorporated into a vest type of garment.

The various constituent elements of the system according to the invention, in particular the electronic measurement device, are specific to the non-destructive testing and are known to the person skilled in the art. The electronic measurement device is thus of the type able to send an excitation signal to the measurement sensor so as to generate a stimulus in the part, and to process and interpret a resulting signal, received in return from the part by the measurement sensor. The electronic measurement device, as well as the measurement sensor to which it is intended to be linked, are designed, in a way that is standard in itself, to allow active measurements of the part's health, i.e. by stimulating the latter and measuring its response to this stimulation, in contrast to a simple passive measurement of a physical characteristic of a material (such as its temperature, thickness, etc.). The electronic measurement device comprises in particular a transmitting part and a receiving part, designed according to the specific type of non-destructive measurement envisaged.

The operator wearing such a garment advantageously no longer needs to carry the constituent elements of the testing system in his arms in order to move and carry out the inspection operations. Both hands remain permanently free to first set the measurement parameters and second hold the sensor while the actual inspection operations are implemented, and at the same time to ensure his safety. The operator's safety and comfort are thus improved, regardless of the external environment, and, as a result, the quality of the inspection measurements is also improved.

According to an advantageous feature of the invention, for each measurement sensor, a connecting cable linking the electronic measurement device and the sensor comprises, at an end to be connected to the sensor, a connector placed on the outside of the vest, preferably on one of its sleeves, and more preferably close to the wrist. Such a feature is particularly advantageous, in particular since it allows the operator, at the time when the inspection operations are to be carried out, to connect the measurement sensor, intended to be held in the hand for taking measurements, as close as possible to the hand.

According to preferred embodiments, the invention also presents the following features, implemented separately or in each of their technically possible combinations.

In preferred embodiments of the invention, the electronic measurement device, electronic card, electrical power supply source and the connecting cables are arranged on a surface, called the inside surface, of the vest, which is defined as the surface intended to be placed facing a user's body, so that these elements are advantageously protected from the external environment.

This invention also advantageously provides for these constituent elements to be distributed on the vest so that the weight to be carried by the user is uniformly distributed.

In this regard, according to an advantageous feature of the invention, the system comprises an adjustment device for adjusting the position of the electrical power supply source in the vest. This device advantageously allows the operator to adjust the position of the power supply source, which is the heaviest element of the system, on the vest according to his particular morphology, and to the configuration of the area to be inspected, so as to provide him with the highest comfort of use. In particular, this device advantageously allows the operator to adjust the position of the electrical power supply source during the inspection, for example to switch it from the back to the front, so as to find the most comfortable position possible for carrying out the inspection.

Preferably, this adjustment device comprises means of guiding the movement of the electrical power supply source between defined positions on the vest, and means for the reversible immobilization thereof in each of these defined positions.

Generally, the constituent elements of the non-destructive testing system according to the invention are chosen so as to present the smallest possible weight, size and electrical consumption.

In preferred embodiments of the invention, the vest comprises an outer cover and a removable inner lining, and the electronic measurement device, electronic card, electrical power supply source and connecting cables are arranged between this outer cover and inner lining.

In order to achieve an objective of the invention, which is to propose a non-destructive testing system having high ergonomics of use, according to an advantageous feature the vest comprises, on a surface called the outside surface opposite an inside surface intended to be placed facing the user's body, a pocket for receiving a viewing and control screen. The vest is also pierced, inside this pocket, by a hole for the passage of a connecting cable linking the screen and the electronic card. The screen, kept in this pocket while moving, is thus easily and directly accessible for the operator wearing the vest when inspection measurements need to be taken. It can then be taken out of the pocket to be used. Preferably, the pocket is provided in its interior with means of protecting the screen. For example, it is padded with foam.

In preferred embodiments of the invention, in a variant to or in association with the above feature, a viewing and control screen is incorporated into a sleeve of the vest, so as to be visible and usable at any time by the operator wearing the vest.

According to an advantageous feature of the invention, the vest comprises, on a surface called the outside surface, a pocket for receiving a measurement sensor, in which the latter can be stored outside the times when inspection operations are implemented.

In preferred embodiments of the invention, the system comprises a plurality of sensors and the vest comprises a plurality of corresponding receiving pockets.

In preferred embodiments of the invention, the system also comprises lighting means arranged on a surface called the outside surface of the vest, preferably on one of its sleeves, so as to provide localized lighting targeted on the inspection site. The lighting means can also, for example, be located on a vest collar to obtain more overall lighting for the user wearing the vest. Such a feature is especially advantageous for an inspection in dark confined areas. These lighting means are preferably controlled by manual means of switching on and off also arranged on an outside surface of the vest, and connected to the system's electronic card for their power supply.

The garment incorporating a non-destructive testing system according to the invention, responding to one or more of the above features, is especially suitable for mobile use. It notably offers the advantage of high ergonomics of use, both for journeys to inspection sites and for carrying out the inspection measurements themselves. It makes it possible to reduce the time required for each test, and notably provides an increased level of safety for the operators and increased reliability for the measurements taken.

BRIEF DESCRIPTION OF THE DRAWINGS

The invention will now be described more precisely in the context of preferred embodiments that are in no way limiting, shown in FIGS. 1 to 3, in which.

DETAILED DESCRIPTION OF THE PREFERRED EMBODIMENTS

The non-destructive testing system according to the invention comprises a vest type of garment 1 in which the various constituent elements of the system allowing inspection measurements to be taken are incorporated.

Figure 1:
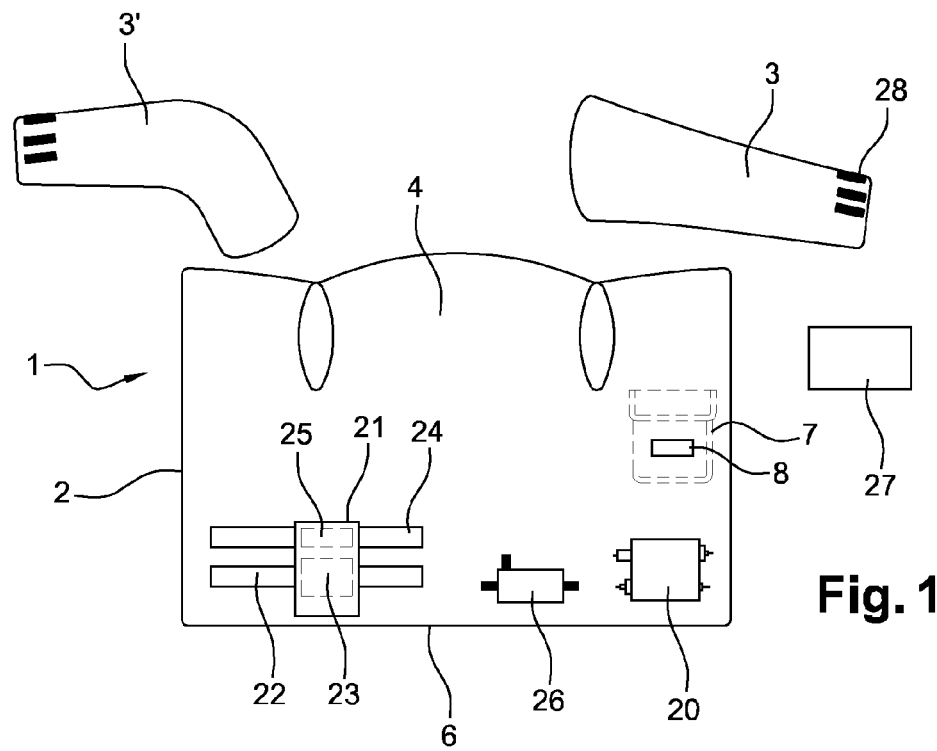
FIG. 1 schematically represents the inside surface of a garment incorporating a non-destructive testing system according to an example of realization of the invention, in an unfolded position, without connecting cables between the various constituent elements.

The vest 1, shown in FIG. 1, comprises a main body 2, intended to cover a user's torso, and sleeves 3, 3'. In this FIG. 1, the vest has been shown flat in an unfolded position, with the sleeves 3 separate from the body 2 for greater clarity.

The body 2 of the vest is in the form of an outer cover made of textile material, preferably an impermeable material with high mechanical resistance and able to dissipate heat. This cover comprises a surface, called the inside surface, 4, which is the surface visible in FIG. 1 and is intended in working conditions to be placed facing the user's body, and an opposite outside surface 5, visible in FIG. 3.

The vest 1 also comprises a removable inner lining, placed facing the inside surface 4 of the outer cover. For reasons of clarity, this inner lining has not been shown in the figures. It is made of a textile material, preferably an aerated material allowing perspiration to be removed.

The constituent elements of the non-destructive testing system allowing test measurements to be taken are incorporated in the vest 1.

Against the inside surface 4 of the outer cover 2, between the latter and the inner lining, an electronic control card 20, or motherboard, an electrical power supply source 21 and an electronic measurement device 26 are fixed.

These elements are advantageously arranged in a distributed way over the width of the vest, as shown in FIG. 1, so as to balance the weight of the vest as well as possible over its whole circumference.

The electronic card 20 is, for example, placed in an inner pocket of the outer cover 2. In general, it is chosen so as to be light and compact, to have low electrical power needs, and to allow multiple connectors to be connected. This electronic card is dedicated to controlling the non-destructive testing electronics, and also to processing the inspection results.

The electronic card 20 is powered electrically by the electrical power supply source, or portable electrical battery 21. The latter is standard in itself, and chosen in accordance with the invention to present the best possible compromise between weight and operational autonomy.

The vest 1 is provided with a device for adjusting the position of the electrical battery 21, which preferably comprises means of guiding the movement of the battery between defined positions against the surface of the outer cover 2, and means of reversible immobilization at each of these positions.

As a non-limiting example, this device comprises a guide rail 22, fixed against the inside surface 4 of the outer cover 2, preferably substantially parallel to a lower edge 6 of the latter, i.e. in a normal position of use for the vest, substantially horizontal. On its face facing the outer cover 2, the battery 21 is equipped with a hook 23 engaged around the guide rail 22, so that it is able to slide along it.

The reversible immobilization of the battery 21 at different positions along the rail 22 is provided by co-operating assembling means fixed on the outer cover 2 and on the battery 21 respectively. These assembling means are notably of the self-gripping type. In the preferred embodiment represented in FIG. 1, the outer cover 2 comprises, always on its inside surface 4, a band 24 of the type with loops or hooks fixed substantially parallel to the rail 22, and preferably covering the latter's entire length. On the underside, the battery 21 is fitted with a band 25 of the type with complementary hooks or loops, allowing it to be fixed in the desired position by simply exerting pressure on it in the direction of the outer cover 2, against the latter.

The vest 1 also comprises an electronic measurement device 26, for example placed in an inner pocket. This device can be of any type known to the person skilled in the art, who will choose it depending on the application in question, associated with one or a plurality of appropriate measurement sensors. In particular, it can be a device for measurement by ultrasound or, for example, by eddy currents. In the context of the invention it is especially advantageous to choose a compact, light electronic device with low power consumption. This electronic device 26 is connected to the motherboard 20, which firstly performs its parameterization and secondly receives the measurement data obtained therefrom. A measurement device such as the one described in patent document FR-A-2 874 689 is in particular especially suitable for use in the context of the system according to the invention.

The system also comprises a control and viewing screen 27, for parameterizing the measurements to be taken by the operator and displaying the results of these measurements.

This screen 27 is placed, relative to the vest 1, so that it can be easily operated by the operator and be visible during the measurement operations.

In variants of the invention, this screen is mobile and linked to the electronic card 20 by a very long cable connection, so that it can be moved a distance away from the vest 1 to ensure convenience of use. On its outside surface 5 the vest 1 is fitted with a pocket 7 to receive the screen, e.g. on the front of the vest on the chest. The screen 27 can be stored conveniently in the pocket 7, from which it is removed when it needs to be used. This pocket is preferably lined with a protective layer, e.g. made of foam.

In other variants of the invention, which are not incompatible with the previous ones, the screen 27 is a flexible and/or touch screen which is incorporated into the outer cover 2, e.g. on one of the vest's sleeves.

The vest 1 also incorporates lighting means, for example in the form of light-emitting diodes 28, which are arranged so as to illuminate the exterior from the outside surface 5 of the vest, preferably at one or each of the two sleeves 3, 3' of the vest, and close to the wrist. These diodes advantageously allow the operator to light the area in which he is taking measurements, near his hand holding the measurement sensor, without generating any particular constraint for him. The diodes 28 are associated to means of controlling their switching on and off, placed close to them, e.g. on the sleeve 3, so as to be easily accessible to the user wearing the vest.

Figure 2:
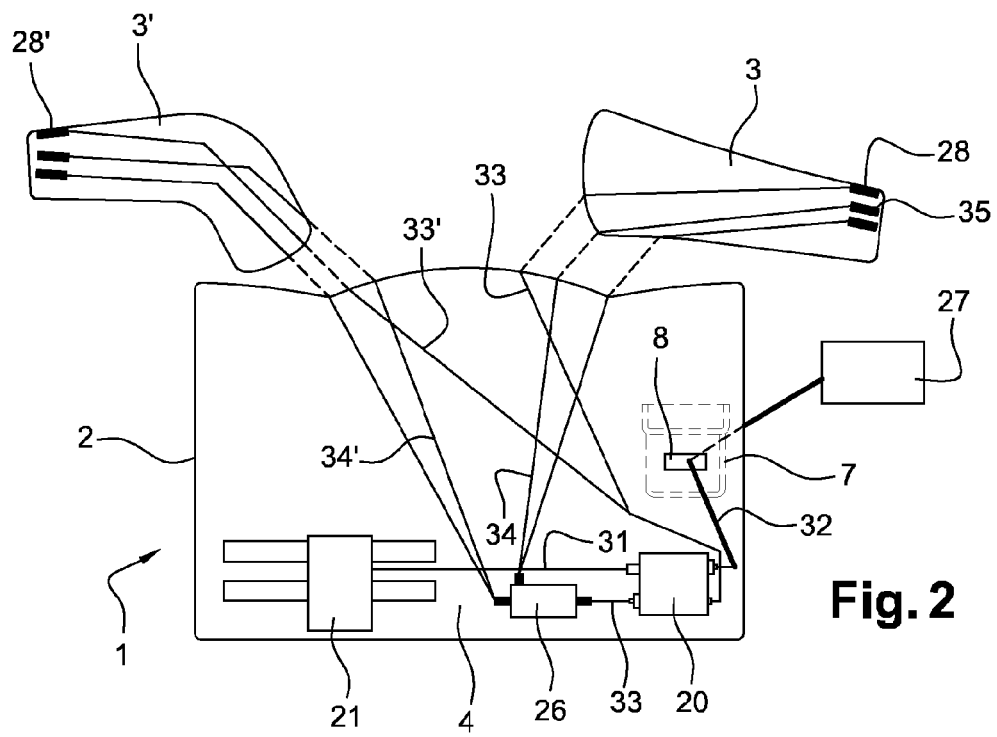
FIG. 2 illustrates the cable links between the various constituent elements of the garment of FIG. 1.

The electrical and electronic connecting cables for connecting the various constituent elements above are shown in FIG. 2. In general, these cables are made of textile materials and are flexible and flat. If necessary, they can be stitched against the inside surface 4 of the outer cover 2, to minimize the risks of deterioration when the vest is handled.

A first cable 31 links the battery 21 to the electronic card 20.

The latter is also linked, firstly, to the screen 27 by a cable 32 and, secondly, to the electronic measurement device 26 by a cable 33.

The outer cover 2 is pierced, inside the pocket 7 receiving the screen 27, by a hole 8 for the passage of the cable 32 from the inside to the outside of the vest.

The electronic card 20 is also linked, by cables 33, 33', to the diodes 28, 28' arranged respectively on the sleeves 3, 3' of the vest.

The whole is completed by at least one cable 34 intended to link the electronic measurement device 26 to a measurement sensor. This measurement sensor, which is not shown in the figures, is standard in itself and chosen according to the application envisaged. It is a handheld type of sensor, i.e. sensors that are held in the hand to bring them close to the area where the test must be carried out. At its end to be connected to the sensor, the cable 34 is terminated by a connector 35 placed on the vest so as to be accessible, for connection, from outside the vest. This connector is preferably placed at a sleeve 3, preferably close to the wrist, i.e. as close as possible to the hand that will hold the sensor during measurement operations.

In preferred embodiments the invention also provides for the electronic measurement device 26 to be associated in this way to a plurality of cables to be linked to measurement sensors, and preferably to cables 34, 34' respectively ending on each of the sleeves 3, 3' of the vest, so as to allow easy use for any operator, whether left- or right-handed.

Figure 3:
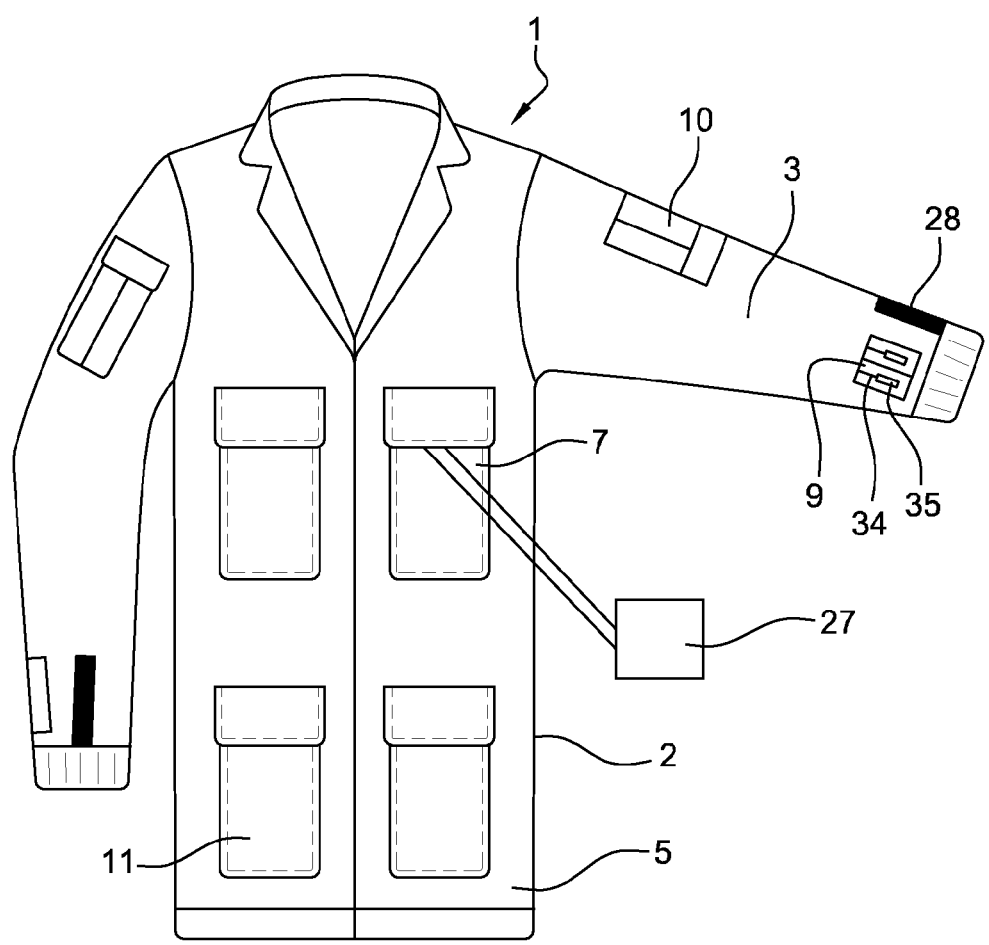
FIG. 3 shows an overall outside view of a garment according to an example of realization of the invention.

The connector 35 has been shown in FIG. 3, which illustrates an example of realization of a vest 1 according to the invention, closed, in an overall view. The connector is visible through a window 9 made in the outer cover 2 on the sleeve 3, at the end of the connecting cable 34.

The vest 1 also comprises on its outside surface 5, preferably on the sleeve 3, as shown in FIG. 3, a pocket 10 for receiving a measurement sensor to be linked to the electronic measurement device 26 at the time of the inspection.

The vest can also comprise other pockets 11, for receiving any other element of use for the inspection, e.g. additional sensors.

With an appropriate choice of the constituent elements, the weight of this vest is limited, and may be as low as 2 kg.

When the operator has to carry out non-destructive testing operations, e.g. measuring the thickness of a part, he puts on the vest 1. His journey to the area where the inspection must be carried out is made easier by the fact that the weight to be carried is distributed around his body. His hands remain free, so that he can easily enter cramped or dangerous areas under improved safety conditions.

The constituent electronic elements of the testing system are also protected between the outer cover and the inner lining of the vest.

When the operator gets ready to take the inspection measurements, he takes the sensor out of its receiving pocket 10 and connects it to the appropriate connector 35. He also takes the control and viewing screen 27 out of its receiving pocket 7 and, after placing it in the most suitable place for its use, he sets the measurement parameters. He switches on the diodes 28, if required, and then he has both hands available to hold the sensor and at the same time ensure his own safety. As the cable 34 for linking the sensor to the electronic measurement device 26 is entirely on the inside of the vest 1, protruding only at the wrist in the window 9, it advantageously does not hinder the operator in his movements. The measurements are thus taken under the best possible conditions, thereby increasing their reliability.

Once the measurements are complete, all that remains is for the operator to put the sensor and screen back in place in the vest and return to the workstation, where the inspection data will be transferred from the electronic card 20 to a computer provided for this purpose.

The above description clearly illustrates that, through its various features and their advantages, the present invention realizes the objectives it set itself. In particular, it provides a non-destructive testing system that, compared to the systems of the prior art, provides improvements in terms of time, safety and comfort for the user, and reliability of the measurements taken.

The invention claimed is:

1. A non-destructive testing system, comprising:
a non-destructive electronic measurement device capable of being connected to a non-destructive measurement sensor,
said non-destructive electronic measurement device configured to generate an excitation signal to be received by said non-destructive measurement sensor so as to generate a stimulus in a part to be tested, and to process and interpret a resulting signal received in return from the part to be tested by way of said non-destructive measurement sensor, and
said non-destructive electronic measurement device being linked to an electronic card that is itself linked to an electrical power supply source and to a viewing and control screen,
said non-destructive electronic measurement device, said electronic card, said electrical power supply source, and said viewing and control screen being electrically and electronically linked by connecting cables,
wherein said non-destructive electronic measurement device, said electronic card, said electrical power supply source, said viewing and control screen, and said connecting cables are incorporated into a vest type of garment, and
wherein said non-destructive testing system also comprises an adjustment device for adjusting a position of said electrical power supply source in said vest, said adjustment device comprising
a movement guide that guides a movement of said electrical power supply source between pre-defined positions on the vest, and
immobilizing means that reversibly immobilizes the power supply source in each of said defined positions,
wherein the movement guide and the immobilizing means are distinct from one another,
wherein the movement guide comprises a guide rail affixed to the vest, and a hook that is affixed to the power supply source and engaged around the rail in a manner such that the power supply source, by way of said hook engaged to said rail, is free to slide along a length of said rail, and
wherein the immobilizing means comprises a first band, affixed to the vest, arranged substantially parallel to the rail and comprising first loops or hooks, and further comprises a second band, affixed to the power supply source, with second hooks or loops adhered thereto and complementary to the first loops or hooks of the first band so as to reversibly adhere to the first loops or hooks of the first band.

2. The system according to claim 1, wherein a connecting cable provided for linking the electronic measurement device and a measurement sensor comprises, at an end to be connected to said sensor, a connector placed on an outside of the vest.

3. The system according to claim 2, wherein said connector is placed on a sleeve of said vest.

4. The system according to claim 1, wherein the electronic measurement device, electronic card, electrical power supply source and the connecting cables are arranged on an inside surface of said vest that faces a user's body.

5. The system according to claim 4, wherein said vest comprises an outer cover and a removable inner lining, and the electronic measurement device, electronic card, electrical power supply source and connecting cables are arranged between said outer cover and said inner lining.

6. The system according to claim 1, wherein the vest comprises, on an outside surface, a pocket for receiving the viewing and control screen, and said vest is pierced, inside said pocket, by a hole for passage of a connecting cable linking said screen and said electronic card.

7. The system according to claim 1, wherein the viewing and control screen is incorporated into a sleeve of said vest.

8. The system according to claim 1, wherein the vest comprises, on an outside surface, a pocket for receiving said measurement sensor.

9. The system according to claim 1, further comprising:
lighting arranged on an outside surface of the vest.

10. The system according to claim 9, wherein said lighting is arranged on a sleeve of said vest.

11. The system according to claim 1, wherein:
a connecting cable provided for linking the electronic measurement device and the measurement sensor comprises, at a sensor end of the connecting cable, a connector placed on the outside of the vest,
the electronic measurement device, electronic card, electrical power supply source and the connecting cables are arranged on an inside surface of said vest that faces a user's body, and
the vest comprises, on an outside surface, a pocket for receiving the viewing and control screen, said vest being pierced, inside said pocket, by a hole for passage of a connecting cable linking said screen and said electronic card.

12. The system according to claim 11, wherein said connector is placed on a sleeve of said vest.

13. The system according to claim 11, wherein said vest comprises an outer cover and a removable inner lining, and the electronic measurement device, electronic card, electrical power supply source and connecting cables are arranged between said outer cover and said inner lining.

14. The system according to claim 11, wherein the viewing and control screen is incorporated into a sleeve of said vest.

15. The system according to claim 11, wherein the vest comprises, on the outside surface, a pocket for receiving said measurement sensor.

16. The system according to claim 11, further comprising:
lighting arranged on the outside surface of the vest.

17. The system according to claim 16, wherein said lighting is arranged on a sleeve of said vest.

18. The system according to claim 1, wherein the adjustment device is configured to adjust a position of the electrical power supply source between a back and a front of the vest.

* * * * *